United States Patent [19]
Piacentino

[11] Patent Number: 4,713,074
[45] Date of Patent: Dec. 15, 1987

[54] IMPLANT DEVICE FOR THE SURGICAL TREATMENT OF INFERTILITY DUE TO OBSTRUCTION OF UTERINE TUBES

[76] Inventor: Renato Piacentino, Viale del Cstello 32, 10024 Moncalieri (Torino), Italy

[21] Appl. No.: 871,785

[22] Filed: Jun. 9, 1986

[30] Foreign Application Priority Data

Jun. 12, 1985 [IT] Italy .............................. 67549 A/85

[51] Int. Cl.⁴ .............................................. A61F 2/04
[52] U.S. Cl. .................................................... 623/12
[58] Field of Search ...................... 623/11, 12, 66, 12; 128/1 R, 200.26; 604/55, 8

[56] References Cited

U.S. PATENT DOCUMENTS

| | | | |
|---|---|---|---|
| 3,334,631 | 8/1967 | Stebletar | 128/200.26 |
| 3,738,365 | 6/1973 | Schulte | 604/8 |
| 4,574,000 | 3/1986 | Hunter | 128/1 R |

FOREIGN PATENT DOCUMENTS 3343248 6/1985 Fed. Rep. of Germany ........ 623/11

OTHER PUBLICATIONS

"Ovarian Implantation into the Uterus (Estes Operation): Clinical and Experimental Evaluation", Yoram Beyth, et al., pp. 657, 660.

Primary Examiner—Richard J. Apley
Assistant Examiner—James Prizant
Attorney, Agent, or Firm—Barnes & Thornburg

[57] ABSTRACT

The device, which is intended to be implanted in a position approximately homologous to the obstructed natural tube to bring the respective ovary closer to the uterus, comprises a generally tubular envelope having a wider portion intended to receive the respective ovary, a narrower portion intended to extend through the wall of the uterus, and a connecting portion interposed between the wider portion and the narrower portion and having a general funnel-shaped configuration converging towards the narrower portion.

12 Claims, 4 Drawing Figures

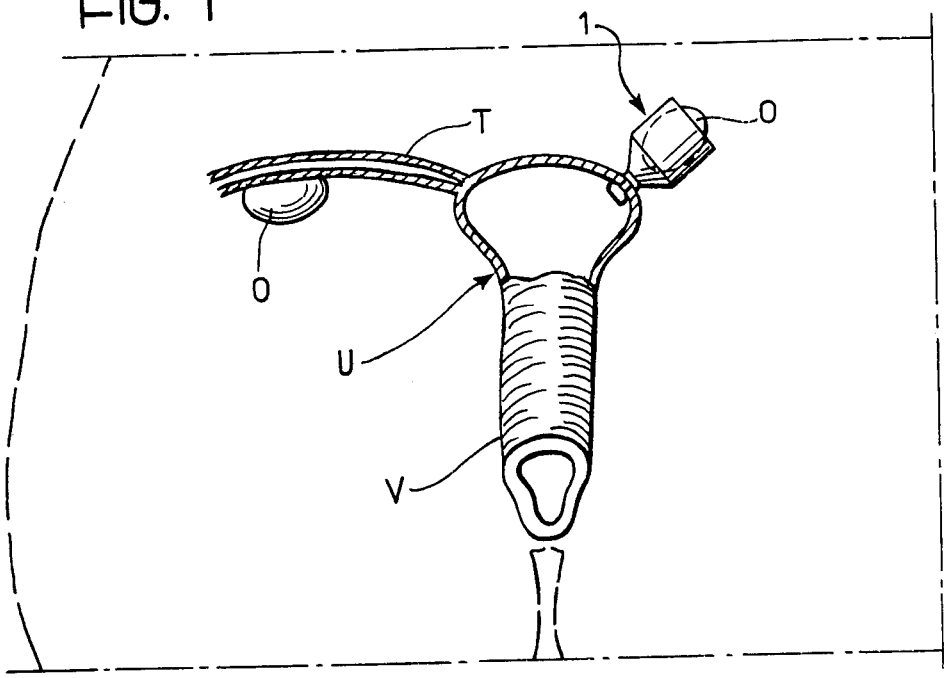
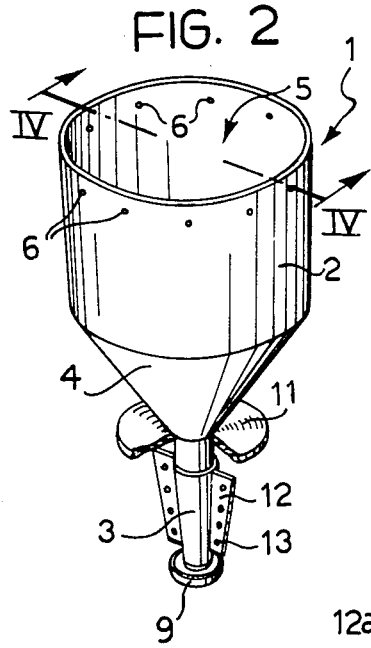
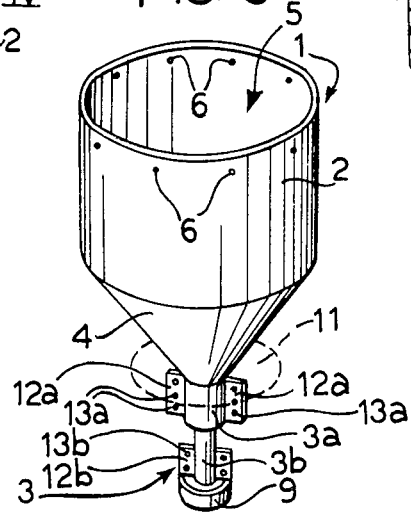
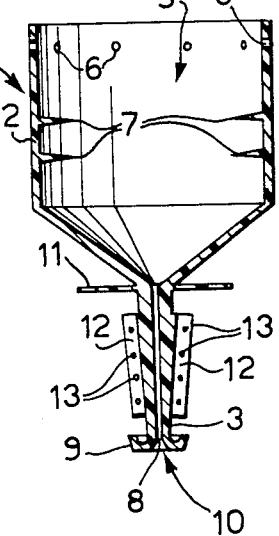

IMPLANT DEVICE FOR THE SURGICAL TREATMENT OF INFERTILITY DUE TO OBSTRUCTION OF UTERINE TUBES

The present invention relates to an implant device for the surgical treatment of female infertility due to tubal obstruction.

"Tubal obstruction" is intended to refer generally to the pathological condition of the female genitalia whereby the tube is not open to oocytes and prevents their migration from the ovary to the uterine cavity. When it assumes a bilateral character, the pathological condition has the unavoidable consequence of infertility (sterility) of the subject affected.

The present invention has the object of providing an implant device usable for the surgical treatment of female infertility due to bilateral tubal obstruction.

This object is achieved by means of a device intended to be implanted in a position approximately homologous to the obstructed natural tube to bring the respective ovary closer to the uterus, characterised in that it comprises a generally tubular envelope having a wider portion intended to receive the respective ovary and a narrower portion intended to extend through the wall of the uterus, and in that the wider portion and the narrower portion are connected together in a general funnel- or cup-shaped configuration converging towards the narrower portion.

The implant device according to the invention is intended to constitute a prosthetic duct which establishes communication between the ovary and the uterine cavity.

Even though the implant device according to the invention is not generally able—except in particular cases—to reproduce the natural mechanism of oocyte migration, it permits a washing liquid introduced into the uterine cavity to reach the ovary and then flow back towards the uterine cavity itself, taking the oocytes with it.

The invention will now be described, purely by way of non-limiting example, with reference to the appended drawings, in which:

FIG. 1 illustrates diagrammatically the inguinal region of the body of a patient in which a device according to the invention is implanted;

FIGS. 2 and 3 illustrate two possible embodiments of the device according to the invention, and FIG. 4 is a section along the line IV—IV of FIG. 2.

An implant device intended to be used for the surgical treatment of female infertility due to bilateral tubal obstruction is generally indicated 1 in the drawings.

For a detailed description of what is meant by tubal obstruction and the consequences of this condition reference is made to the specialised literature on the subject.

For the purposes of understanding the present invention, it will be sufficient to recall that tubal obstruction is intended to refer to the pathological condition of female genitalia whereby the tube is not open to oocytes and prevents their migration from the ovary to the uterine cavity.

The device 1 according to the invention is intended to be implanted in the position shown diagrammatically in FIG. 1.

In this figure, which illustrates the main elements of the female genitalia, the uterus is generally indicated U, from which there extend, downwardly, the vagina V and, in an upper and lateral position, the tubes T leading each to a respective ovary O.

The relative dispositions of the right-hand tube T and ovary O prior to the implantation of the device according to the invention are shown on the left-hand side of FIG. 1.

The right-hand side of the Figure, however, shows the device according to the invention implanted in a position approximately homologous to the left-hand natural tube which has been removed so as not to be visible in the drawing.

The left-hand ovary O, however, has been moved from its natural position, it being brought close to the uterus U and inserted within the device 1.

This device has an overall tubular structure in which there can be distinguished a wider portion 2 and a narrower portion 3 separated by an intermediate connecting portion 4.

Seen as a whole, therefore, the device 1 has a general funnel- or cup-shaped configuration.

The wider portion 2 defines an internal chamber 5 with dimensions such as to be able to accommodate the ovary O which has been moved from its natural position.

In a form of embodiment considered preferable at present, the wider portion 2 is constituted by thin-walled cylindrical body having a diameter of about 25-45 mm (preferably about 25 mm) and a height, measured in the axial direction with respect to the device 1, of about 30 mm.

At the end opposite the narrower portion 3, the wall of the wider portion 2 may have through-holes 6 which permit the device 1 to be fixed in the implant position by sutures.

Preferably, however, the wall of the wider portion is made of a "soft" material (such as Daflon) which permits the wall to be passed through by sutures enabling the device 1 to be fixed in the implant position.

Internally, in a projecting position with respect to the chamber 5, the wall of the wider portion 2 may be provided with pointed projections 7 the function of which will be better described below.

In the embodiment illustrated, the intermediate portion 4 is constituted by a conical wall the generatrices of which are inclined by about 45° to the axis of the cylindrical wall of the wider portion.

Naturally, the functional aspects of the device being retained, it will be possible to adopt different configurations, for example, to achieve a more gradual connection between the wider portion 2 and the narrower portion 3.

The narrower portion is passed through by an axial cavity 8 whose sectional area descreases gradually from the intermediate connecting portion 4 to the free end of the narrower portion 3 itself.

In correspondence with the free end, the axial cavity 8 has a terminal aperture with radial dimensions of the order of 2-4 mm.

The terminal aperture is surrounded by an annular body 9 defining an enlarged mouth portion 10 which is generally flared.

At the opposite end, that is, the end facing the intermediate portion 4, the narrower portion 3 has a collar 11 made of soft and/or flexible biocompatible material.

Generally, the device 1 as a whole is made from a rigid or semi-rigid biocompatible material, such as, for example, polytetrafluoroethylene (PTFE) moulded or subjected to mechanical working, in the portions 3 and 4, and of a soft material, such as Daflon, in the portion 2. The connection between the soft portion 2 and the rigid portions 3, 4 may be effected by various techniques. For example, it is possible to effect the connection with stitches passing through holes provided in the flared edge of the portion 4.

The collar 11 may form an integral part of the body of the device 1 or constitute an accessory intended to be fitted onto the body of the device.

In the first case, the required softness or flexibility may be imparted to the collar 11 by making the element with a reduced wall thickness. In the case in which an accessory element is used, however, it is also possible to make the collar 11 using a fabric of biocompatible material, such as a fabric made from the material known under the trade name of Delrin.

The two embodiments illustrated in FIGS. 2 and 3 (in the latter the profile of the collar is shown by a broken line) differ essentially in that the narrower portions 3 have different structures.

In the embodiment of FIG. 2 (to which the sectional view of FIG. 4 also relates), the narrower portion 3 is constituted substantially by a tubular element from which extend two diametrally-opposed radial tabs 12 with holes 13 which enable the device 1 to be fixed to the wall of the uterus by sutures.

In the embodiment of FIG. 3, the narrower portion 3 comprises two tubular elements, indicated 3a and 3b respectively, which are joined together telescopically.

The element 3a is connected to the connecting portion 4 and has respective tabs 12a with holes 13a for the passage of sutures.

The element 3b, which defines the free end with the flared mouth 9, slides within the element 3a and, to advantage, is also provided with tabs 12b with holes 13b for the application of sutures.

In the implant position referred to diagrammatically in FIG. 1, the narrower portion 3 of the device is inserted into the wall of the uterus (myometrium) in such a manner as to pass through it.

In particular, the enlarged mouth portion 10 faces into the uterine cavity. The edges of the annular body 9 defining the enlarged mouth extend radially over the internal surface of the myometrium (endometrium), preventing the axial opening 8 from being obstructed as a result of the cyclic growth of the endometrium itself.

The collar 11, however, rests on the outer surface of the myometrium (perimetrium) and helps to maintain the orientation of the device 1 in the implant position.

The device 1 is fixed in this position by means of sutures applied to the wall of the uterus and passing througha the holes 13 or 13a and 13b of the tabs 12 or 12a and 12b.

The length of the narrower portion 3 (between the enlarged mouth portion 9 and the collar 11) is typically of the order of 25 mm, a dimension which corresponds to the typical thickness of the myometrium.

In the case of the embodiment of FIG. 3, the length of the narrower portion 3 can be adapted with accuracy to the anthropometric characteristics of the patient by sliding the two telescopically-coupled elements 3a, 3b longitudinally one with respect to the other.

The ovary O which was previously joined to the obstructed tube T is introduced into the chamber 5 defined by the wider portion 2 (which is fixed in the implant position by sutures passing through the wall of the portion 2 itself).

In the implant position, the axial cavity of the device 1 constitutes an open duct which establishes communication between the ovary and the uterine cavity, allowing oocytes to migrate towards the uterine cavity itself.

In general, since the device according to the invention is not able to reproduce the typical peristaltic movements of the natural tube, it is not possible to expect a spontaneous migration of oocytes towards the uterine cavity.

Such a result may be obtained, however, by cyclically subjecting the patient in which the device according to the invention is implanted to uterine washes with physiological solutions. These solutions are able to enter the chamber 5 in which the ovary O is situated through the axial cavity 8 of the narrower portion 3 and then flow back into the uterine cavity, drawing therewith the oocytes collected in chamber 5.

The pointed projections 7 might possibly promote the breaking of the follicle during ovulation to prevent the formation of ovarian cysts.

Naturally, the principle of the invention remaining unchanged, the details of realization and the forms of embodiment may be varied widely from that described and illustrated, without thereby departing from the scope of the present invention.

I claim:

1. An implant device for the surgical treatment of infertility due to obstruction of uterine tubes, intended to be implanted in a position approximately homologous to the obstructed natural tube to bring the respective ovary closer to the uterus, comprising a generally tubular envelope having a wider portion intended to receive the respective ovary and a narrower portion intended to extend through the wall of the uterus, said narrower portion having a length corresponding substantially to a thickness of the wall of the uterus, said wider portion and said narrower portion being immediately adjacent one another and connected together in a general funnel-shaped configuration converging towards said narrower portion.

2. A device according to claim 1, wherein said narrower portion is provided, at the end opposite said wider portion, with an enlarged mouth portion which opens towards the wall of the uterus in the implant position.

3. A device according to claim 2, wherein said mouth portion is generally flared.

4. A device according to claim 1, wherein said narrower portion comprises at least two elements joined together telescopically, whereby the length of said narrower portion is selectively adaptable to the thickness of the wall of the uterus.

5. A device according to claim 1, wherein said narrower portion has an axial cavity whose sectional area decreases gradually away from said wider portion.

6. A device according to claim 1, wherein said narrower portion has an axial cavity which has diametral dimensions of the order of 2-4 mm at the end opposite said wider portion.

7. A device according to claim 1, wherein said narrower portion has associated therewith tab means extending in a substantially radial direction relative to the device and having holes for the fixing of the device in the implant position by sutures.

8. A device according to claim 1, wherein said narrower portion has associated therewith a collar member which rests on the outer surface (perimetrium) of the wall of the uterus in the implant position.

9. A device according to claim 8, wherein said collar member is substantially flexible.

10. A device according to claim 1, wherein said wider portion is provided internally with pointed projections able to promote the breaking of the follicle during ovulation.

11. A device according to claim 1, wherein said wider portion has holes for the fixing of the device in the implant position by sutures.

12. A method for the surgical treatment of infertility due to tubal obstruction, comprising the steps of:

removing at least one of the ovaries from its position, separating it from its respective tube;

implanting in a position approximately homologous to the respective tube an implant device comprising a generally tubular envelope with a wider portion and a narrower portion joined together in a generally funnel-shaped configuration converging towards the narrower portion, arranging said narrower portion in a position in which it extends through the wall of the uterus and said wider portion outside the uterus, said narrower portion having a length corresponding substantially to a thickness of the wall of the uterus, and disposing said at least one ovary inside the wider portion of the implant device such that the ovary is moved closer to the uterus.

* * * * *